(12) United States Patent
Vidal-de-Miguel et al.

(10) Patent No.: US 8,247,764 B2
(45) Date of Patent: Aug. 21, 2012

(54) METHOD AND APPARATUS TO SHARPLY FOCUS AEROSOL PARTICLES AT HIGH FLOW RATE AND OVER A WIDE RANGE OF SIZES

METHOD AND APPARATUS TO SHARPLY FOCUS AEROSOL PARTICLES AT HIGH FLOW RATE AND OVER A WIDE RANGE OF SIZES

CROSS REFERENCE TO RELATED APPLICATION

This application claims the benefit of priority to U.S. Provisional Patent Application No. US61/131,878, filed on Jun. 13, 2008.

U.S. PATENT DOCUMENTS CITED

U.S. patent application Ser. No. 12/012,771, by J. Fernandez de la Mora, with priority date of 5 Feb. 2007

U.S. Pat. No. 4,383,171; Sinha; M. P., Giffin; C. E., Norris; D. D., Friedlander; S. K, Particle analyzing method and apparatus, May 10, 1983

U.S. Pat. No. 5,270,542; P. H McMurry; D. B. Kittleson; P. J. Ziemman; P. Liu, Apparatus and method for shaping and detecting a particle beam; Dec. 14, 1993.

U.S. Pat. No. 6,040,574, Jayne; John T., Worsnop; Douglas R., Kolb; Charles E., Atmospheric-particle analyzer, Mar. 21, 2000

OTHER PUBLICATIONS CITED

[1] Robinson, A. On the Motion of Small Particles in a Potential Field Flow, Communications in Pure and Applied Mathematics, IX, 69-84 (1956).

[2] Chen B. T., Yeh H. C., Cheng Y. S., Performance of a modified virtual impactor, Aerosol Science. & And Technology., 5(3), 369-376, 1986

[3] Romay, F. J., Roberts, D. L., Marple, V. A., Liu, B. Y. H., and Olson, B. (2002). A High Performance Aerosol Concentrator for Bioaerosol Agent Detection, Aerosol Sci. Technol. 36:217-226.

[4] Willeke, K., and Pavlik, R. E. (1978), size classification of fine particles by opposing jets, *Environ. Sci. Technol.* 12:563-566.

[5] Willeke, K, and Pavlik, R. E. (1979). *J. Aerosol Sci.* 10:1.

[6] Fernández de la Mora, J. & Riesco-Chueca P. (1988) *Aerodynamic focusing of particles in a carrier gas.* J. Fluid Mech. 195, 1-21.

[7] Israel, G. W. and Friedlander, S. K. (1967) High Speed Beams of Small Particles, *J. Coll. Interface Sci.*, 24, 330-333.

[8] Dahneke. B. E and Friedlander, S. K. (1970) Velocity Characteristics of Beams of spherical Polystyrene Particles, *J. Aerosol Sci.*, J, 325-339.

[9] Cheng, Y. S., and Dahneke, B. E. (1979). *J. Aerosol. Sci.* 10:363-368.

[10] Dahneke, B. (1978). Aerosol Beams, in Recent Developments in Aerosol Science (D. T. Shaw, ed.) John Wiley & Sons, New York, chapter 9.

[11] Dahneke, B. E. and Cheng, Y. S. (1979) *J. Aerosol Sci.*, 10, 257-274.

[12] Dahneke, B. E., Hoover, J. and Cheng, Y. S. (1982) *J. Coll. Interface Sci.*, 87, 167.

[13] Sinha, M. P., Griffin, C. E., Norris, D. D., Estes, T J., Vilker, V. L. and Friedlander, S. K. *J. Coll. And Interface Sci.*, 87, 140-152 (1982).

[14] Sinha, M. P. and Friedlander, S. K. *J. Colloid and Interface Sci.*, 112,573-582 (1986).

[15] Fernández de la Mora, J. (1996). Drastic improvements on the resolution of aerosol size spectrometers via aerodynamic focusing: The case of variable-pressure impactors. Chemical Engineering Communications, 151, 101-124.

[16] Piseri, P., Tafreshi, H. V., and Milani, P. (2004). Manipulation of Nanoparticles in Supersonic Beams for the Production of Nanostructured Materials, *Curr. Opin. Solid State and Materials Sci.* 8(3-4): 195-202.

[17] Fernandez de la Mora, J. (2006) Aerodynamic focusing in spatially periodic flows, J. Aerosol Science, 37 (3): 323-339

[18] Friedlander, S. K. Smoke, Dust and Haze, Section 4.6, Wiley, New York (1977).

[19] Rao, N., Navascues, J. and Fernandez de la Mora, J. (1993) Aerodynamic Focusing of Particles in Viscous Jets, J. Aerosol Sci., 24, 879-892.

[20] Fuerstenau, S., Gomez, A., and Fernandez de la Mora (1994) J. Visualization of Aerodynamically Focused Aerosol Jets, *J. Aerosol Sci.*, 25, 165-173.

[21] Middha, P. and Wexler, A. S. (2003) Particle Focusing Characteristics of Sonic Jets, Aerosol Sci. & Tech., 37:907-915,

[22] Maxey, M. R. (1987) The motion of small spherical-particles in a cellular-flow field, *Phys. Fluids,* 30, 1915-1928.

[23] Ganan-Calvo, A. M. & Lasheras, J. C. 1991 The dynamics and mixing of small spherical particles in a plane free shear layer. Phys. Fluids A 3, 1207-1217.

[24] Tio, K.-K., Ganan-Calvo, A. M. & Lasheras, J. C. 1993a The dynamics of small heavy rigid spherical particles in a periodic Stuart vortex flow. Phys. Fluids A 5, 1679{1693.

[25] Tio, K.-K., Linan, A., Lasheras, J. C. & Ganan-Calvo, A. M. 1993b On the dynamics of buoyant and heavy particles in a periodic Stuart vortex flow. J. Fluid Mech. 254, 671-699

[28] Liu P., Ziemman, P. J. Kittelson, D. P. & McMurry, P. H. (1995a) Generating Particle Beams of Controlled Dimensions and divergence: I. Theory of particle Motion in Aerodynamic Lenses and Nozzle expansions, Aerosol Sci. and Tech., 22,293-313

[29] Liu P., Ziemman, P. J. Kittelson, D. P. & McMurry, P. H. (1995b) Generating Particle Beams of Controlled Dimensions and divergence: I. Experimental Evaluation of particle Motion in Aerodynamic Lenses and Nozzle expansions, Aerosol Sci. and Tech., 22,293-313

[31] Kasparian J, Boutou V, Wolf J P, Pan Y L, Chang R K (2007), Single-particle laser-induced-fluorescence spectra of biological and other organic-carbon aerosols in the atmosphere: Measurements at New Haven, Conn., and Las Cruces, N. Mex., G, Geoph. Res. Atmos. 112 (D24) Article Number: D24S19

[32] Liu, P., Ziemann, P. J, Kittelson, D. P. and McMurry, P. H. (1993) Aerodynamic Lenses for Producing Particle Beams of Controlled Dimensions and Divergence. pp. 119-135 in *Synthesis and characterization of ultrafine particles*, J Marijnissen and S. Pratsinis editors; Delft University Press.

[33] William S. Saric; GORTLER VORTICES; Mechanical and Aerospace Engineering, Arizona State University, Tempe, Ariz. 85287-6106

[34] Davitt K, Song Y K, Patterson W R, Nurmikko A V, Pan Y L, Chang R K, Han J, Gherasimova M, Cobler P J, Butler P D, Palermo V, (2006) Spectroscopic sorting of aerosols by a compact sensor employing UV LEDs, Aerosol Sci & Tech., 40 (12), 1047-1051

FIELD OF THE INVENTION

This invention relates to an apparatus and a method for sharply focusing a broad size range of particles suspended in a gas, while avoiding the seriously limiting inability of prior art to do so at relatively high flow rates (Reynolds number). This new focusing device enables improvements in a wide range of other devices, including virtual impactors and aerosol concentrators.

BACKGROUND OF THE INVENTION

It is often desirable to sample and concentrate particles suspended in a gas for further analysis or detection. Unlike a liquid or a low speed gas flow where the fluid density is relatively constant, the flow of particles suspended in a gas can be rendered highly compressible by inertial effects (Robinson, 1956, Michael, 1968)[1]. As a result, the number of particles per unit volume n at a particular location in the flow may be substantially higher than its initial value $n_o$ at a reference point upstream. The concentration factor defined as $$C = n/n_o \qquad (1)$$

may therefore be much larger than unity, a situation of great practical interest to increase the sensitivity of instruments used for particle detection or analysis. Indeed, since the volumetric sampling flow rate q of such instrument is generally fixed, their sensitivity is increased by a factor C if the particles are concentrated by that factor before being sampled. The usefulness of such a concentrating operation is evident in many situations. For instance, to detect minute quantities of suspended explosive particles at a security control (see U.S. patent application Ser. No. 12/012,771), to monitor the level of cleanness in a room where devices sensitive to particle contamination are being processed, etc.

Figure 1:
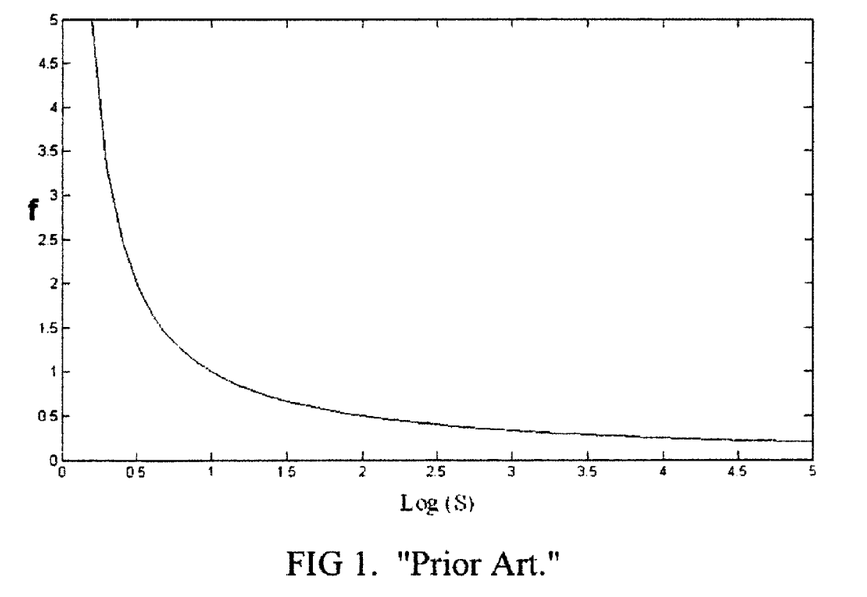
FIG. 1 ("Prior art") shows schematically the dependence f(S) of the focal distance f (normalized with the nozzle throat diameter) on the Stokes number S for particles accelerated through a focusing contraction with d>>1.
Figure 2:
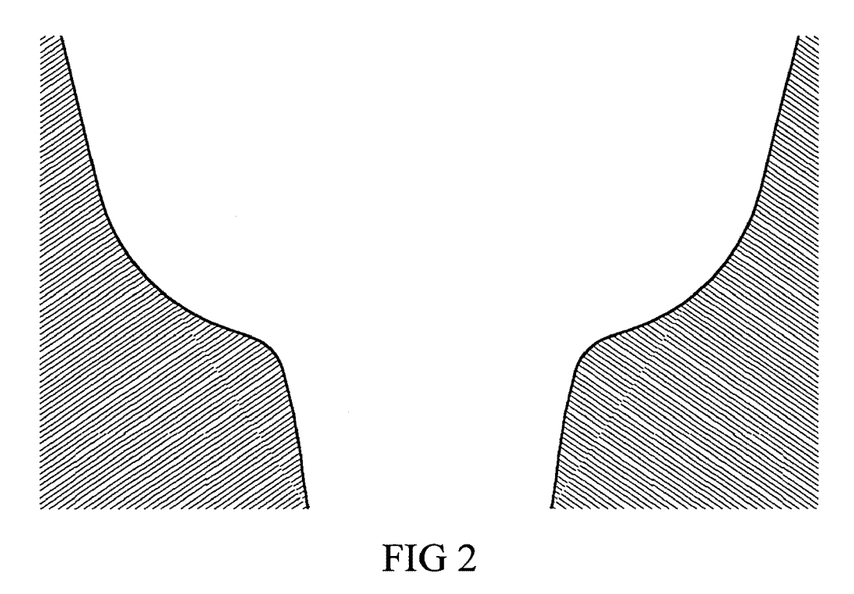
FIG. 2 represents a section of a preferred shape of an individual focusing contraction.

Under practical situations involving detection or analysis of ambient particles, many particle instruments sample flows typically of 1 lit/min, sometimes considerably more. If one's goal is to concentrate ambient particles by a factor of 1000 prior to detecting them in such instruments, the concentrating device needs to handle very high flow rates of thousands of liters/min. The concentrating device to achieve this goal must therefore be capable of working at very high Reynolds numbers, Re, which for a jet of velocity U formed by a nozzle of diameter D is defined in terms of the fluid's kinematic viscosity v as:

$$Re=DU/v. \qquad (2)$$

Virtual impactors are common instruments (Chen et al. 1986)[2] that can be used as particle concentrators (Romay et al., 2002)[3]. They involve a jet of gas carrying particles, forced to impact against a virtual wall. The virtual wall is not a solid wall, but an imaginary interface separating the jet from another fluid stream. This second fluid stream is most commonly a confined region of slow moving gas, often a cavity, but it could also be a second relatively strong jet (Willeke and Pavlik, 1978, 1979)[4, 5]. This virtual wall ideally deflects the majority of the impinging gas jet, but is penetrated by some of the suspended particles. In principle, none of the jet gas but some of the particles could be admitted into the cavity region, in which case C would be infinite. In practice, the virtual wall is most often fluid-dynamically unstable and it is conventionally stabilized in virtual impactors by accepting steadily a finite flow rate q of gas into the cavity of slow moving gas. The required minor to major flow ratio q/Q is typically larger than 3%, so that the maximum value of C achievable for particles transferred with high efficiency is generally less than 30. Note that this circumstance not only limits the concentrating ability of virtual impactors. It also reduces considerably their resolving power with respect to that of conventional wall impactors. The reason is that impactors normally capture large particles and not small particles, yet, virtual impactors capture also at least a fraction q/Q of the small particles, and therefore they depart from the ideal high-pass filter impactors they are supposed to be.

An alternative to a single virtual impactor would be a set of m virtual impactors in series, where the limiting concentration factor $C_1$ of a single virtual impactor is raised to the power N of the number of stages: $C_N=C_1^N$. This approach has been demonstrated by Romay et al. (2002) [3] for the case of two sequential stages of virtual impaction. One problem with the multistage concentrator is that the largest particle size it can pass is limited by particle impaction in the lines connecting one stage to the next.

One of the most effective schemes known to concentrate aerosol particles is so called aerodynamic focusing (Fernández de la Mora and Riesco-Chueca, 1988) [6]. The present invention is therefore concerned with aerosol concentrators hybrid between focusing devices and virtual impactors. The term aerodynamic focusing will be used here to refer to situations leading to relatively large C values. The pioneering ideas leading to the notion of aerodynamic particle focusing are due to Israel and Friedlander (1967) [7], with extensions by Dahneke and Friedlander (1970) [8], Cheng & Dahneke (1979)[9]; Dahneke (1978) [10], Dahneke & Cheng (1979) [11], Dahneke, Hoover, & Cheng (1982) [12], Sinha et al. (1982) [13], and Sinha and Friedlander (1986) [14]. This early work is further described in U.S. Pat. No. 4,383,171, with extensions up to 2006 summarized in Fernández de la Mora (1996) [15], Piseri et al. (2004)[16], and Fernández de la Mora (2006) [17]. In the pioneering work by the groups of Friedlander and Dahneke, and in the most recent developments from McMurry and colleagues, the primary concern was to separate aerosol particles from the gas carrying them, in order to introduce the particles into a vacuum system for further analysis, most often by mass spectrometry. Several characteristics of the earlier manifestations of focusing were that (i) they involved the expansion of a gas into a vacuum; (ii) most of the separation between the gas and the particles occurred in a supersonic jet; (iii) the nozzles used to initiate this supersonic expansion were slowly converging; (iv) the sampling of the particle beam took place many nozzle diameters downstream from the supersonic nozzle; (v) the width of the particle beam obtained was not substantially smaller than the diameter of the sonic nozzle. Consequently, the term focusing could not be used in the absolute sense defined here ($C>>1$), but only in a relative sense comparing particle concentrations to gas concentrations. In other words, the particles kept approximately their initial concentration (or decreased it moderately), while the concentration of gas molecules diminished greatly. The term focusing could however be used in the different sense that, as shown by Friedlander and colleagues, the particles in the beam did cross from one side of the symmetry axis to the other.

The first demonstration of focusing in the specific sense of interest to this invention ($C>>1$) was given by Fernández de la Mora and Riesco-Chueca (1988) [6]. (i) They showed that focusing can occur also in subsonic and low speed flows, and may arise as a true singularity, with C tending to infinity. This singular effect, however, is limited by so-called geometric aberration, due to the fact that the point at which particles of a given size cross the axis of symmetry varies slightly as a function of their initial distance to the axis of symmetry. (ii) They demonstrated practical situations with $C>1000$. (iii) They showed that the slowly converging nozzles used previously had poor performance, while nozzles with more rapidly converging walls (including wedges with half angles $\alpha>\pi/2$) could focus substantially smaller particles. (iv) They introduced the concept of the critical focusing Stokes number $S_{crit}$, above which particles initially near the axis would cross the axis, noting that subcritical particles do not cross the axis, critical particles cross it at infinity, and supercritical particles cross it at finite distances from the nozzle. FIG. 1 shows schematically in a standard scientific convention the evolution of said finite distance as a function of the Stokes number. The logarithm of the Stokes (Log(S)) is represented in the axis of abscissas while the distance at which particles cross the axis of the nozzle (f) is represented in the axis of ordinates.

The Stokes number S is here defined conventionally as (Friedlander, 1977) [18]

$$S = \tau U/D, \qquad (3)$$

based on jet speed U, nozzle diameter D and the stopping time $\tau$ of a particle. $\tau$ is defined as the time required to reduce the speed of the particle by a factor of e (Euler's number) when flying though gas at rest. In this context it is also useful to define the aerodynamic size of a particle as the diameter of a spherical particle whose resistance to motion in the gas is linear with its velocity relative to the gas, and whose density and stopping time $\tau$ are the same as those for the real particle The contributions of Fernández de la Mora and Riesco-Chueca (1988) [6] were primarily theoretical, with additional numerical examples restricted to two-dimensional flows. However, the general validity of their picture has been confirmed by experiments with axisymmetric nozzles (Rao et al, 1993 [19], Fuerstenau et al., 1994[20]). Easily fabricated thin-plate orifice nozzles ($\alpha = \pi/2$) have subsequently been most often used for aerodynamic focusing. However, Mihda and Wexler (2003) [21] have confirmed the advantage of even larger convergence cone angles, while both these authors and Piseri et al (2004) [16] have contributed improved geometries capable of focusing particles with unusually small Stokes numbers.

While useful to concentrate sharply particles within a narrow range of sizes (Stokes numbers S), the work of Fernández de la Mora and Riesco-Chueca (1988) did not solve the problem of concentrating simultaneously a wide range of particle sizes, which is the concern of the present invention. An important step in that direction came from two independent lines of work, based on many (rather than just one) acceleration and deceleration steps. This scheme will be referred to as multiple shot focusing. As shown by Robinson (1956) [1], one suitably designed stage of acceleration and deceleration leads to a net concentration, $C_1 > 1$. For small S, $C_1$ differs only slightly from unity. But a sequence of N such steps in series produces a concentration factor $C = C_1^N$, leading at sufficiently large N to a highly concentrated or "focused" aerosol, even at modest S values. This behavior was first seen in some striking calculations by Maxey (1987) [22] involving spatially periodic flows, which have inspired a large number of subsequent fluid dynamical investigations (i.e., Gañán-Calvo & Lasheras, 1991[23]; Tio, Liñán, Lasheras, & Gañán-Calvo, 1993[24, 25]; Martin & Meiburg, 1994[26]; Rubin, Jones, & Maxey, 1995[27], among many others). This rich line of theoretical work has had no observable effect on practical aerosol concentrators. Multiple shot focusing was first brought to practice in general as well as introduced conceptually in the aerosol literature by McMurry and his colleagues (Liu et al. 1993, 1995a, 1995b [28, 29]), without connection to Maxey's precedent. These authors used primarily sharp edge orifice nozzles, and introduced the widely accepted terminology aerodynamic lens to refer to each individual nozzle followed by a deceleration region. Their work has had considerable impact on the important problem originally addressed by Friedlander and Dahneke: determining the chemical composition of suspended particles after introducing them into a vacuum.

Some of these ideas have been protected in U.S. Pat. No. 5,270,542. This patent is restricted to situations where there is a relatively rapid lateral expansion of a gas accompanied by a relatively slow lateral expansion of the aerosol particles. Since it is not possible to achieve such a rapid expansion of a gas under subsonic or even moderately supersonic conditions (except under very small Reynolds numbers that would severely restrict the usefulness of the invention), the U.S. Pat. No. 5,270,542 patent addresses exclusively situations initiated by the formation of a highly supersonic jet. Other related patents exist, similarly restricted to form particle beams for introduction into a vacuum, such as U.S. Pat. No. 6,040,574. Highly supersonic jets are indeed unavoidable when introducing an aerosol initially at atmospheric pressure into a vacuum. But they are undesirable in applications such as those pursued here, where the process of particle concentration tends to take place close to the original pressure of the gas-particle suspension (often atmospheric pressure). Even under conditions where a moderately supersonic jet is advantageous, the present invention considers only initial expansion ratios $p_o/p_1$ for the jet pressure of at most 10.

From the point of view of the present invention, the main advantage of multiple shot focusing with approximately periodic nozzles is the considerably wider range of S values that can be focused (typically from S below 0.1 up to above 1), and the higher concentration factor C generally achievable, compared to what is possible with single shot focusing. The multiple shot approach is in principle not restricted to the formation of aerosol beams for introduction into a vacuum. However, in practice, it is not readily extended to applications involving atmospheric pressures and high gas flow rates. The reason is that the flow configurations so far employed or proposed lead to transition to turbulence and make the focusing devices inoperative at relatively low Reynolds numbers. For instance, according to Eichler et al. (1998; FIG. 5), the focusing performance of the nozzle geometry most commonly used in aerodynamic lenses (a sharp edge orifice) degrades rapidly at Re above 70. The 5,270,542 patent describes four different types of focusing lenses, all of which lead to detachment and reattachment of the streamlines (Liu et al. 1995a, b). As is well known to those skilled in the art, these configurations can be stable only at relatively low Re. This restriction is generally compatible with particle beam forming applications, but can be readily seen to be inadequate for most atmospheric pressure applications. For instance, for air at ambient conditions, with a nozzle diameter D=1 mm, the flow rate at Re=70 is Q=0.33 lit/min.

Some remarks are pertinent here on solutions previously proposed to match a receiving tube or collector and an incoming jet in an aerosol concentrator. Both virtual impactors and the various skimmer designs used for introducing focused aerosol beams into a final vacuum stage have the same configuration of a jet impinging on a plate or a cone with an aligned orifice. This is a special case of a flow past a cavity with a free shear layer at the virtual wall, which is subject to a Kelvin-Helmholtz type instability with feedback due to the mobile stagnation point at the border of the cavity. As a result, there is a net oscillatory penetration of gas jet into the cavity. The aerodynamic configuration in the collector cavity needs to be sufficiently stable to enable safe passage of the smallest particles in the range of interest into the steady region of the cavity. In the case of virtual impactors, the instability is solved via a relatively high suction through the collector orifice, which limits the concentration factor C. In beam forming devices, the instability is resolved by two circumstances: First, the Reynolds number is already relatively low through the focusing region. Second, it becomes even smaller in the low pressure region at which the beam is admitted to the high vacuum region of the device. But this solution is inevitably associated to low flow rates.

The advantages in this respect of a focusing virtual impactor have been noted by Fuerstenau et al. (1994) [20]. If the accelerating nozzle concentrates the particles into a region of diameter $d_f$ substantially smaller than the nozzle throat diameter D, the collector orifice diameter $d_c$ can be made comparable to $d_f$. This reduces the flow Reynolds number in the region of the sampling orifice by a potentially large factor $(d_c/D)^2$. The reason is that the characteristic length is reduced by the factor $d_c/D$, while the flow velocity in this region (stagnation point flow region when there is little or no suction) is also reduced by another $d_c/D$ factor. Unfortunately the potential advantage noted by Fuerstenau et al. (1994) [20] is restricted to single shot focusing, which can by its very nature concentrate only a relatively modest range of particle sizes. It could via multiple shot focusing be turned into a particle concentrator of wide size range, but only at flow rates too small to meet our present objectives.

In conclusion, there are presently no known solutions to the related problems of achieving (i) virtual impactors with sampling flow ratios q/Q smaller than 1%
(ii) single-stage virtual impactor concentrators with C>100
(iii) multiple shot focusing concentrators achieving C>100 at Re>100
(iv) focusing devices with a wide particle size range operating at Re>100

Furthermore, the only aerodynamic concentration scheme known to achieve C>100 at high Re (Romay et al. 2002) [3] uses at least two conventional virtual impactors in series. But this system is limited in the largest particle size it can handle by particle losses on the flow lines leading from the first to the second virtual impactor stage.

SUMMARY OF THE INVENTION

One first goal of this invention is to develop a focusing device concentrating highly a wide range of particle sizes (wide S range) and operating at high flow rates (high Re). The requirement of focusing a broad range of particle sizes demands the use of more than one focusing nozzle. But the turbulent transition problem characteristic of all prior focusing lenses (at all but relatively small values of Re) requires the development of a new aerodynamic configuration avoiding entirely flow detachment. This is not possible in the periodic or quasiperiodic acceleration-deceleration schemes of Maxey (1987) [22] or Liu et al. (1993) [31, 32], since the converging accelerating region must, in each period, be necessarily followed by a diverging decelerating region, which is always unstable at high Re.

The new scheme must therefore focus the broad particle size range of interest in a continuously converging geometry. A single convergence can focus sharply only a narrow range of particle sizes, so the present invention relies on a ladder of contractions, each of which focuses a progressively smaller range of particle sizes, without defocusing appreciably the larger particles previously concentrated.

A sectional view of a preferred embodiment of the new focusing element acting as the elementary step in this ladder is shown in FIG. 2, and will subsequently be referred to as a contraction. Although this invention is not restricted to axisymmetric situations, the flow in the contraction of FIG. 2 comes from a circular section of diameter $d_i$ and ends in a circular section with a smaller diameter $d_{i+1}$. The contraction is therefore characterized by its shape, its length, and the diameter ratio d:

$$d=d_i/d_{i+1}. \quad (4)$$

The continuously converging geometry described in FIG. 2, with controlled inflexions and moderate radii of curvature, is designed such that boundary layer separation is avoided. Note the need to sidestep two types of instabilities characteristic of contractions. These are most readily visualized in the case of a contraction with sharp steps. First, the flow tends to separate on the corner where the wall first ceases to be cylindrical and begins to converge radially. This problem is associated to the instability of the decelerating (actually stagnating) boundary layer forming as the corner is approached axially from upstream. The result is a recirculation region at the corner, with vortices that can be periodically swept by the flow. Such so-called Goertler [33] vortices tend to form not only in stepped geometries, but also in improperly designed smooth shaped contractions typical of the inlet region of wind tunnels. The second problem is even more serious, and is associated to the singularity of the fluid velocity formed at the end of the step, when the wall ceases to be radial and turns again into an axial direction. The flow then simply separates, and another recirculating region forms between the separated jet and the wall. When this second step is rounded off slightly, the sharp turn forced into the flow creates a region of relatively high velocity, whereby the flow needs to decelerate downstream from the corner, leading similarly to boundary layer separation. This problem eventually disappears as the corner curvature is decreased, and the wall geometry is suitably designed downstream from it.

In order to promote focusing effects, it is desirable to make the geometry of the contraction as abrupt as possible. On the other hand, a stable aerodynamic configuration calls for smooth geometries. A contraction must therefore be abrupt enough to produce focusing effects with relatively low Stokes numbers, but smooth enough to avoid Goertler vortex formation and flow detachments downstream of the rounded corner region producing high velocities zones. The geometry shown in FIG. 2 meets these requirements, but other related geometries can be devised by those skilled in the art, and are also included in this invention.

Some of the contractions needed for this invention must have a different dependence of the focal distance f versus S compared with conventional focusing elements. Both have a critical S value, $S_{crit}$, at which the focal distance tends to infinity. For $S>S_{crit}$, the beam of particles takes approximately the shape of a sand clock constriction. For greater precision, the focal distance f(S) is defined here as the distance between the neck of a particle beam of fixed S and a reference position (the same for all contractions when several are put in series, for instance, the throat of the contraction located most downstream). For a conventional focusing lens, characterized by d>>1, f decreases monotonically at increasing S (FIG. 1). In contrast, for the alternative contraction of interest to this invention, where d is of order unity, f(S) exhibits a characteristic minimum at a certain $S_m>S_{crit}$. (FIG. 3). The qualitative interpretation of this result is that there is a certain band of S values, centered at $S_m$, which is well tuned to the contraction, and is focused effectively (as indicated by their moderate focal distance). Substantially larger or smaller S values focus much less efficiently, as indicated by their large focal distances. We shall subsequently refer to these lenses as narrow band or band lenses. Their novelty does not reside in their inefficient focusing of small particles (small S), but on their inefficient focusing also of large particles (S>>1). A second important feature of band lenses follows from the minimum arising in the f(S) curve, which makes the focal point relatively independent of S in the vicinity of $S_m$. This effect is crucial for the design of a series of wide range focusing contractions, and deserves some discussion.

Note first that the band focusing phenomenon is favored by values of d of order unity. In a conventional aerodynamic lens, where d>>1, two undesirable things tend to happen. First, particles with S>>$S_{crit}$ have a long convergence path over which they can accelerate to relatively high radial speeds, in spite of their high inertia (sluggishness). Consequently they cross the axis at a focal point, and tend to open up radially downstream from it, landing at the end of the process closer to the wall of the aerodynamic lens than they were initially. This is the overfocusing or defocusing phenomenon discussed by Liu et al. for S larger than a certain value $S_m$. As a result, a succession of lenses is useful only to concentrate particles for which S<$S_{max}$. This overfocusing effect is evidently moderated or even eliminated when d ceases to be large, since particles with high S have no time to acquire sufficient radial speeds. The second important difference between conventional lenses and band lenses is analogous to the first, but involves the particle velocity in the axial direction. At d>>1, axial flow velocities right before the contraction are very small (the initial axial velocity is proportional to $1/d^2$), so that large particles tend to spend plenty of time in the contraction region, which favors overfocusing. However, when d is of order unity, the large particles have a substantial initial axial velocity, and can cross the contraction region in a relatively short time. In other words, the large particles are entrained through the contraction by their initial axial velocity, without any significant focusing or defocusing. The net result of this entrainment effect is that large particles are not defocused in a contraction suitable to sharply focus smaller particles. The fact that lenses with a moderate contraction ratio d do not defocus particles with high S values, and may even focus them slightly, has been previously reported in the case of moderately corrugated periodic nozzles (Fernández de la Mora, 2006[17]). This prior art, however, cannot achieve the high Reynolds numbers of interest to the present invention. Wide particle size range focusing at high Re is based in this invention on a series of contractions, each of which focuses sharply the band of particle sizes it is designed to concentrate, without appreciably defocusing the various bands of progressively larger particles previously focused by prior contractions. This avoidance of overfocusing is a necessary condition for success; but it is not sufficient. In addition, all particle sizes in a wide range must have closely matched focal points. The strategy to achieve this goal is discussed next.

Figure 3:
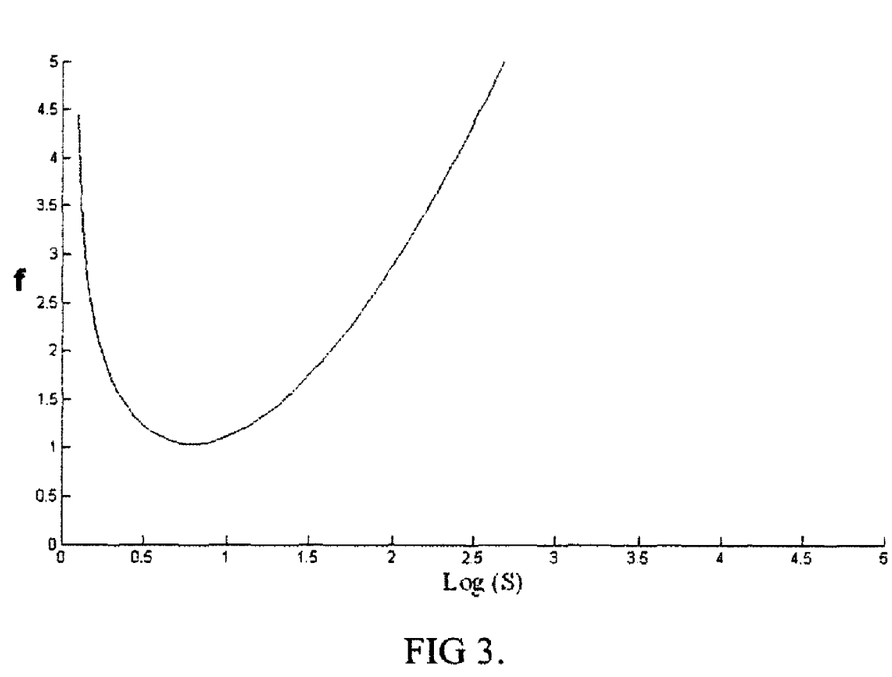
FIG. 3 shows schematically an f(S) curve for particles accelerated through a focusing contraction having d comparable to unity.
Figure 4:
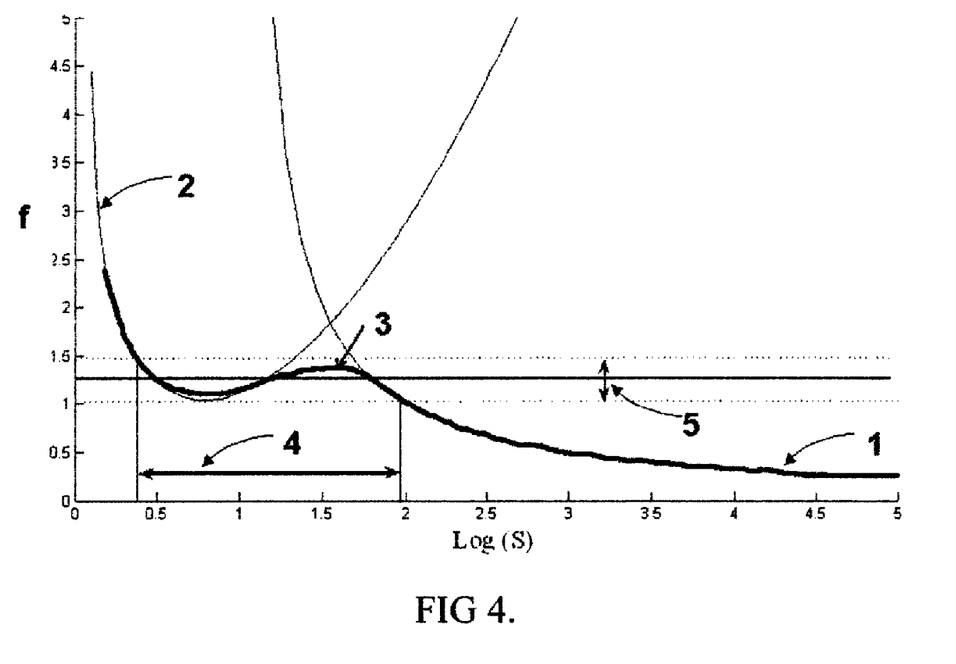
FIG. 4 shows schematically an f(S) curve for particles accelerated first through a contraction with d>>1, and then through a second contraction with d comparable to unity.
Figure 5:
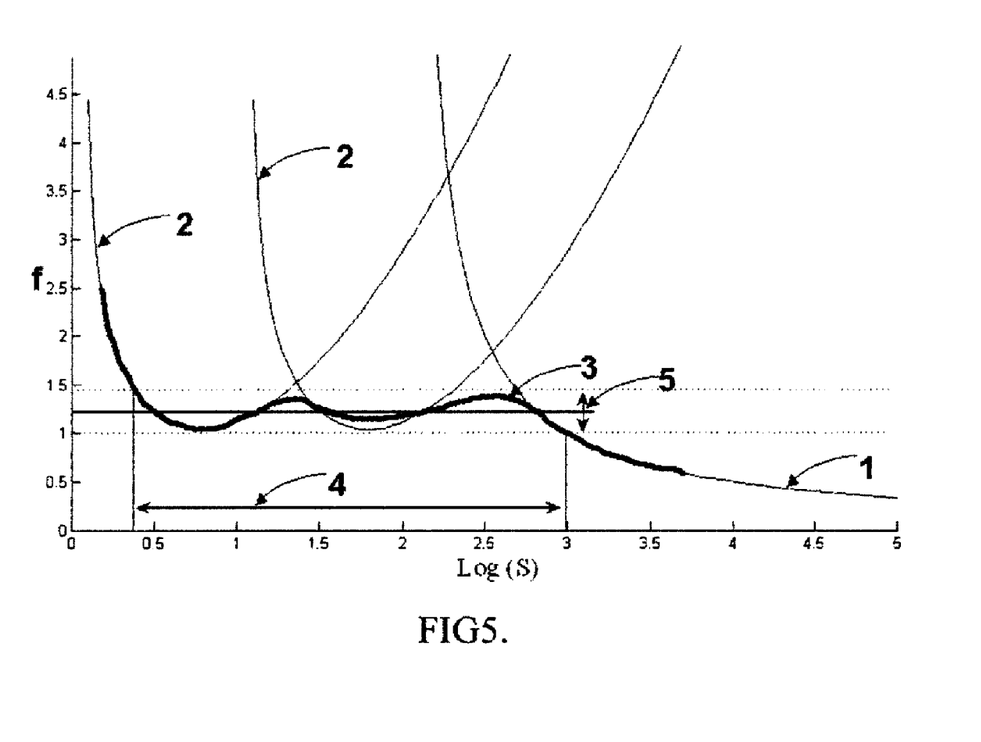
FIG. 5 shows schematically the f(S) curve for particles accelerated first through a contraction with d>>1, and then through two additional contractions having d values comparable to unity.
Figure 6:
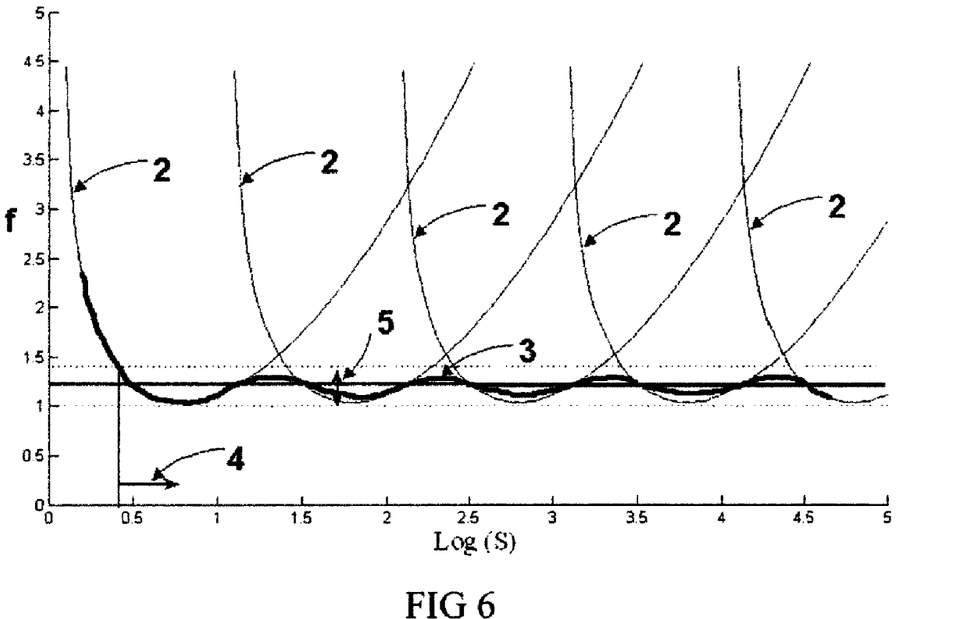
FIG. 6 Shows schematically the f(S) curve for a composite focusing nozzle formed by a sequence of N consecutive contractions.

FIG. 4 illustrates qualitatively the f(S) response of two successive contractions. The one most upstream has relatively large d and entry diameter. It therefore focuses particles with a relatively large S, and is characterized by the monotonically decreasing (FIG. 1 like) f(S) curve shown to the right (1). The second contraction has a moderate d value, associated with the f(S) curve characterized by the band focusing (FIG. 3 like) shown to the left (2). The f(S) curve resulting from coupling both contractions in series is shown qualitatively in FIG. 4 as a hybrid of the other two curves (3). The hybrid f(S) curve (3) resulting from placing in series three contractions is similarly shown in FIG. 5. The wavy pattern seen in FIGS. 4 and 5 permits having a broad range of S values (4) focused within a relatively narrow axial region (5). Clearly, as illustrated in FIG. 6, each additional contraction stage added leads to a new wave in the composite f(S) curve (3), further extending the range of Stokes numbers (4) that can be narrowly concentrated at a common focus (5). Achieving a common focus is non-trivial because the composite desired custom f(S) curve is affected by interactions between the various $f_i$(S) curves (2) for each individual stage. But various iterations of fine tuning of the parameters d and the longitudinal distances characterizing the various contractions permits achieving the goal of minimizing the vertical amplitude of the waves (variation of focal distance), and controlling its mean position and the length of the wavy region (range of Stokes numbers focusable). For instance, (i) the mean value of f(S) in the range of S associated to one contraction is decreased by increasing its length. (ii) Also, the useful range of S and the amplitude of a wave associated to one contraction is decreased by decreasing the associated parameter d.

Figure 7:
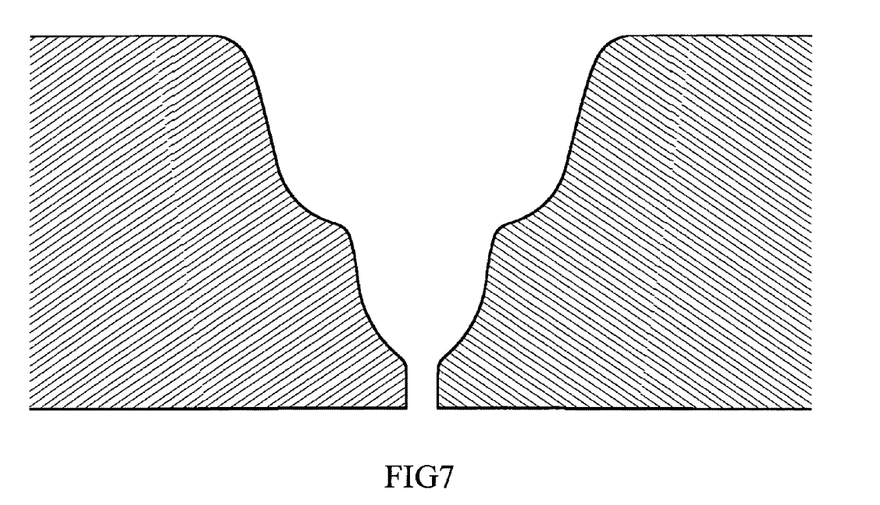
FIG. 7 shows a meridional section of the preferred shape of a composite focusing nozzle formed by a series of three axisymmetric contractions, and capable of focusing a wide range of particle sizes at a high Reynolds number
Figure 8:
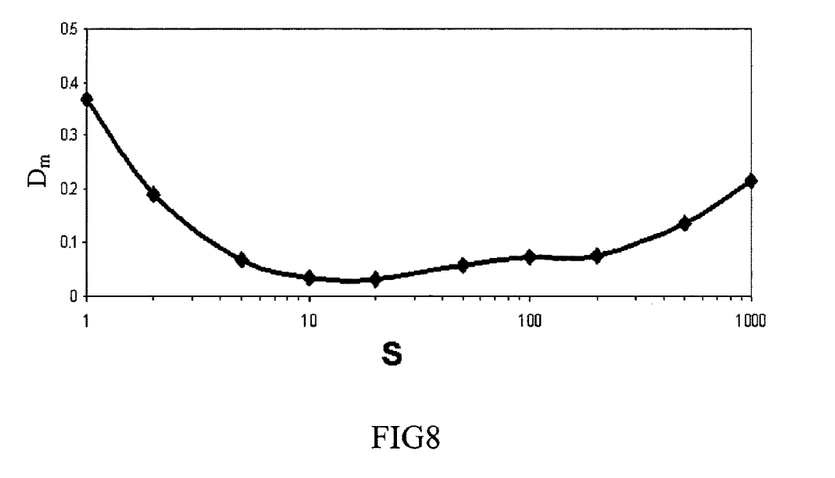
FIG. 8 represents the diameter of the neck of the focused beam (normalized with the nozzle throat diameter) formed by the composite focusing nozzle of FIG. 7 at a fixed axial position, as a function of S. This is a result of fluid and aerosol computations for Re=7000, and a realistic nonlinear aerodynamic drag law valid for particle Reynolds numbers below 800.

FIG. 7 shows a meridional section of a preferred embodiment of a series of three axisymmetric contractions specially designed to maintain an almost fixed focal distance through a wide range of S. FIG. 8 represents, in a standard scientific plot, the corresponding diameter of the neck of the focused beam ($D_m$), normalized with the nozzle throat diameter, at a fixed axial position, as a function of S. In this case, with only three contractions, a range of almost three orders of magnitude in S is concentrated at a radius 20% of the nozzle throat radius. Many other designs with two or more contractions and different sets of axial and radial distance parameters as well as different individual contraction geometries can be designed by those skilled in the art, and are also included in this invention.

One application among others of a composite focusing nozzle with stabilized f(S) curve is to use it in a focusing virtual impactor that would have the advantages already noted by Fuerstenau et al. and would in addition overcome the limitation in the limited range of particle sizes.

Coupling a composite focusing nozzle with a collector to make a focusing virtual impactor brings together the advantages of permitting high flow rates (high Re), and high concentration factors (C) over a wide range of particle sizes. A brief discussion on the parameter $\Delta=d_c/D$ defining the geometric relation between the diameters of the composite focusing nozzle throat (D) and the collector orifice ($d_c$) in the virtual impactor becomes now necessary. For simplicity, the discussion will be made in terms of diameters because the discussion is facilitated in the case of cylindrically symmetric geometries. But the invention is not limited to nozzles of circular cross section, and can be readily generalized to other nozzle and collector orifice geometries. Looking at FIGS. 4 to 6, and assuming that the parameter $\Delta$ is larger than the diameter of the neck of the focal region (both normalized with the nozzle throat diameter), one sees that a particle will be captured most efficiently when its focal distance is close to the position of the collector orifice. When the focal distance is not exactly at the position of the collector, particles can still be totally captured as long as the collector's orifice is big enough to capture the whole converging or diverging beam. As $\Delta$ grows, the allowed range of focal distances totally captured grows too. Maintaining the focal distance stable for a wide range of Stokes, permits combining low values of $\Delta$ with high capture efficiencies over that wide range of Stokes, provided that the collector orifice is located near the position of the stable focus. Such low values of $\Delta$ help stabilize the collector's cavity while decreasing q/Q. As a result, a high Reynolds number, and a high concentration factor can be achieved over a wide S range.

An optimal design of the ratio $\Delta$ is most helpful. Small values of $\Delta$ will require a sharper focus. This will tend to increase the size of the smallest particle that can be transmitted, and will put more restrictions on the design of a composite focusing nozzle suitable to smooth the wavy pattern shown in FIGS. 4 to 6. At the same time, the biggest particle transmitted will be limited, since the particles must be smaller than the collector orifice, not only to be collected, but also to avoid blocking it. On the other hand, large values of $\Delta$ will promote undesirable aerodynamic instabilities, which, as already noted, would either limit the Reynolds number of the impinging jet, or decrease C. In conclusion, one wants to make $\Delta$ as wide as possible to increase the focusing performance, but not so much to promote instabilities that would harm the sampling performance.

A MORE DETAILED DESCRIPTION OF THE INVENTION

The composite focusing nozzle already described can be used in a variety of ways according to the present invention. It can be used without further additions to concentrate narrowly into a focal region the particles suspended in a large sampled flow rate of gas. These particles can then be interrogated optically, for instance to determine if they contain dangerous pathogens (Kasparian et al. 2007[31]; Davitt et al. 2006[34]). Alternatively, the focused particle beam can be impacted on a surface for various purposes. For instance, to write a narrow line, to alter this surface as a result of the spatially concentrated high-speed impact of relatively hard particles, to cut the surface, etc. Higher particle velocities may be achieved without degrading the focus by extending longitudinally the final nearly cylindrical region of the last nozzle section, as in a gun, keeping it slightly conical to provide acceleration to maintain the laminar flow. While a comparable result may be achieved by means of a single-shot focusing nozzle with particles of uniform size, the use of several contractions in series permits focusing particles with a broader size distribution, which can generally be procured more economically.

Figure 9:
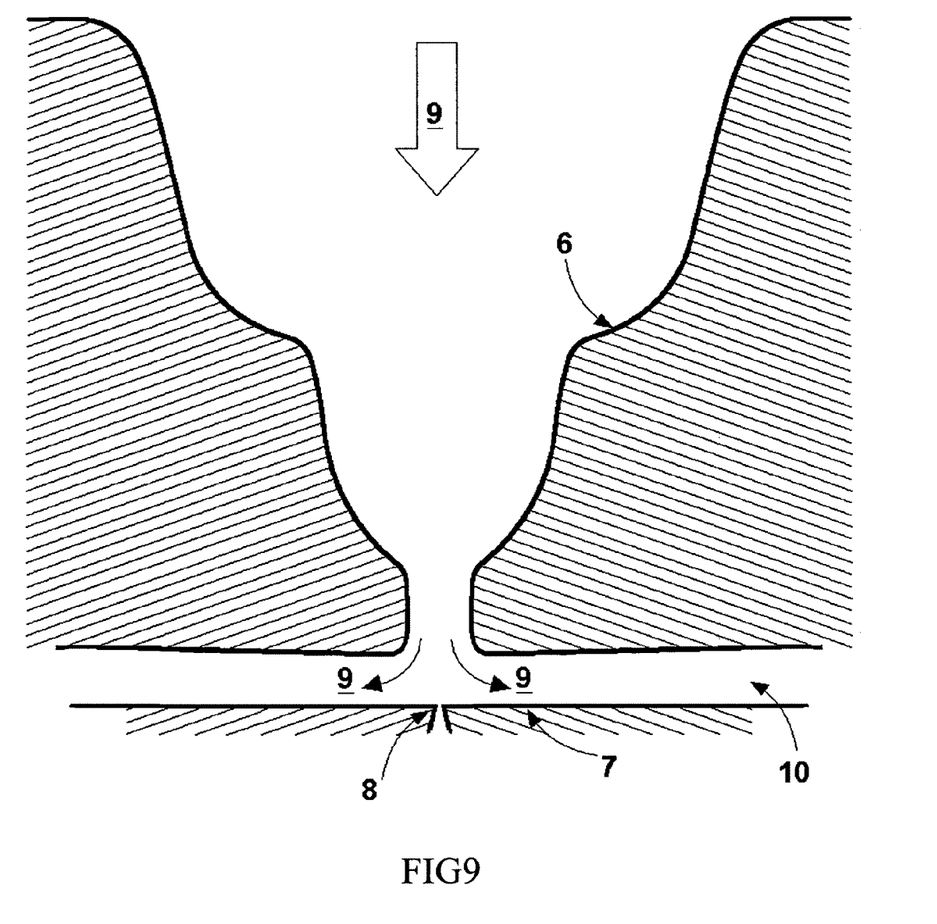
FIG. 9 illustrates the coupling of the composite focusing nozzle of FIG. 7 with a collector having a centered sampling orifice.
Figure 10:
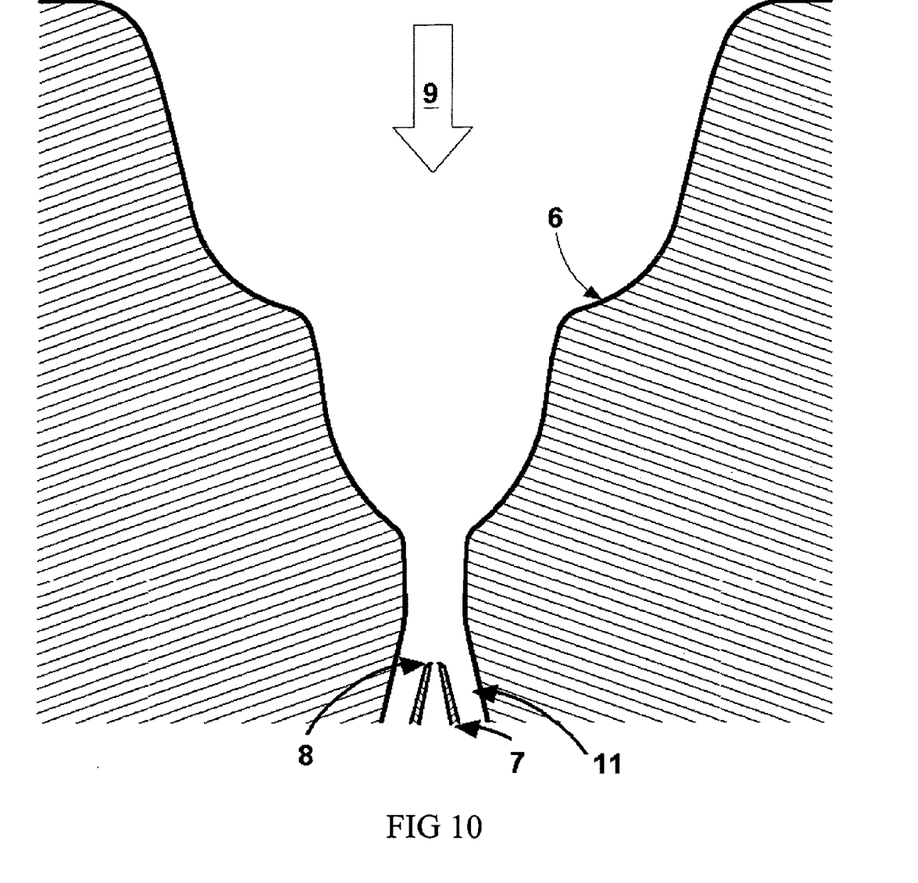
FIG. 10 illustrates the coupling of the composite focusing nozzle of FIG. 7 with a relatively thin collector having a centered sampling orifice, including a diffuser geometry for pressure recovery.

The composite nozzle described can also be used as the focusing component of a focusing particle concentrator. One embodiment of this device is illustrated in FIG. 9, including the composite nozzle described (6) and also a large collector piece (7) with a centered inlet hole (8). In this case, the major flow (9) is deflected radially, and should preferably be subsequently passed through a radial diffuser (10) for pressure recovery. As illustrated in FIG. 10, the major flow can alternatively be guided axially around a small collector by an axial diffuser (11), in order to recover the pressure drop resulting from accelerating the gas through the series of contractions. Note that FIGS. 9 and 10 only differ in the shape of theirs collectors and diffusers. For a given pump capacity, the diffuser permits reaching higher gas speeds in the jet.

A small portion of the jet flow (the minor flow) is sampled through the centered hole in the collector (8), at a flow rate controlled downstream of this hole. Due to their high inertia, the particles having been focused in the composite focusing contractions are not deflected by the plate. Accordingly, those focused particles confined within a radius smaller than the collector radius will penetrate through it. All the particles in a prescribed size range can in fact penetrate if the hole in the collector is made slightly larger than the width of the focused particle beam. For instance, according to FIG. 8, any particle with Stokes ranging from 2 to 300 will enter a collector orifice 1/10 of the nozzle diameter.

The fraction of the gas flow sampled through the holes in the designs of FIGS. 9 and 10 can be substantially smaller than in a conventional virtual impactor, because the flow in the virtual wall is now far more stable as a result of the smaller sampling hole (8). The concentration factor achievable in this device is accordingly considerably larger than in existing virtual impactors.

Some of the particles sampled will remain in suspension, and can be used in aerosol form as in conventional virtual impactors. Some of the largest particles may impact in the internal walls of the collector chamber. In some cases, these particles can be evaporated in situ by heating the chamber walls, and the vapors released can be carried away by the minor gas flow into a suitable analyzer, such as an ion mobility spectrometer, a differential mobility analyzer (DMA, such as those described in U.S. Pat. Nos. 5,869,831, 5,936,242 or 6,787,763), or a mass spectrometer. Notice that this process can be continuous, unlike the more common scheme of collecting inertially the particles from a large flow on a collector surface for a certain period, and then releasing their vapors on a small gas flow that conveys them into an analyzer.

In order to produce even higher concentrations of aerosol, the minor flow can be further concentrated in a second stage, which could be similar to the first focusing concentrator of this invention, or could be a conventional virtual impactor. If the Reynolds number in this second stage is sufficiently small, it could be based on an apparatus suitable for low Reynolds focusing, relying for instance on a series of contractions and expansions.

Note that the present invention is not necessarily restricted to atmospheric pressure operation, but includes flows at reduced pressures in either the first stage of focusing, or other stages, including those acting on the minor flow.

Other improvements may be added. For instance, in order to protect the collector orifice from being obstructed by very large particles, a cyclone, a sieve, or some other device for selective elimination of large particles can be positioned at a desired location in the system.

Figure 11:
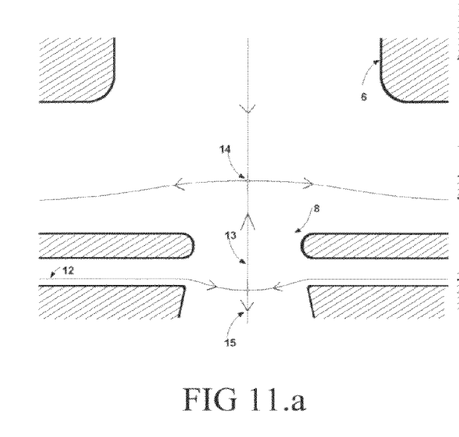
FIGS. 11a and 11b illustrate schematically a detail of the collector orifice with two different counterflow configurations with different lengths.

A further improvement of the concentrator device, also included in this invention uses counterflow gas rather than suction in the collector orifice, as shown in FIG. 11. FIG. 11 shows in detail the collection orifice (8) including counterflow gas to stabilize the fluid configuration. The outlet of the composite focusing nozzle (6) is shown at the top. Counterflow gas is introduced through a lateral slit (12). A fraction of the gas introduced (13) through the lateral slit (12) is accelerated through the collecting orifice (8) against the mayor flow (9) and impacts against it forming a stagnation point (14). Said stagnation point (14) is sufficiently separated from the walls of the collector to prevent cavity instabilities, but sufficiently close to them so that viscous effects damp and stabilizes fluid dynamic perturbations. Another fraction of the gas introduced (15) though the slit can be driven downstream with the minor flow in order to carry the collected particles, which can cross the counterflow region practically undisturbed due to their high inertia. This approach serves to stabilize the virtual wall, in a manner similar to that of the opposed jets of Willeke and Pavlik. However, the much smaller counterflow jet used here remains necessarily close to the collector wall and is further stabilized by viscous forces. Because the sampling of minor flow is now relieved from performing its former stabilizing function, it can be chosen freely, for instance, to achieve concentration factors as high as desired. In the configuration of FIG. 11.a, the focused particles entering the orifice from the jet region need to have a certain minimal inertia to be able to penetrate through the counterflow gas region. This will not be a problem since the particles entering the collector orifice have been previously focused, and therefore have sufficient inertia (S~1) to penetrate through a quiescent region of dimensions of the order of D.

The configuration of FIG. 9 can be used alternatively to create an improved virtual impactor, termed a focusing virtual impactor. The advantages to be gained from incorporating a focusing stage in a virtual impactor are in part similar to those of the focusing wall impactors of Fernandez de la Mora (1996) [15], where focusing brought all particle streamlines close to the axis of symmetry, greatly increasing the resolution of the impactor. A further improvement of this performance also included in this invention would entirely eliminate entry of incompletely focused particles, thereby yielding a sharp response of the instrument (zero transmission below a critical S and near unity transmission above it). The operation of this virtual impactor is illustrated in FIGS. 11a and 11b. In this case, the collector orifice (8) does not ingest gas, but actually blows out a small counterflow of gas. The line leading from the orifice into the interior of the cavity is slightly conical, such that focused particles entering through the orifice with a direction slightly different from that of the axis of symmetry do not impact on the walls. The counterflow gas is introduced into this conical outlet line at an intermediate position, such that part of the gas injected goes towards the cavity, and the other portion constitutes the counterflow gas moving towards the impaction region. In this configuration, the focused particles entering the orifice from the jet region need to have a certain minimal inertia to be able to reach the interior of the cavity traveling against the counterflow gas. By increasing the flow rate of this gas, or by making a longer counterflow throat (16) as in FIG. 11.b, one can exclude from the cavity larger and larger particles. Above a certain flow rate of counterflow gas, the only particles admitted are those with large enough S to be fully focused into the orifice of the collector. By operating at this or a larger flow rate, the desired condition of full transmission for large particles and zero transmission for small particles is obtained.

Figure 12:
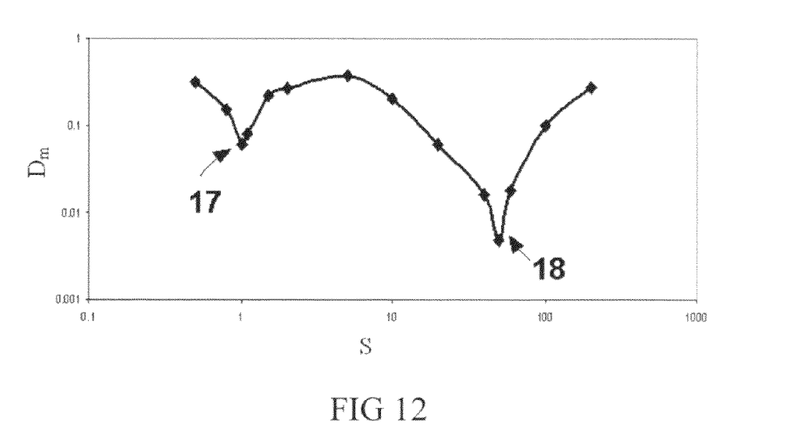
FIG. 12 represents the diameter of the focused beam (normalized with the nozzle throat diameter) at a fixed axial position, as a function of S. The beam is formed by a composite focusing nozzle designed with two contractions specially arranged to produce a sharp focus.

Virtual impactors are useful not only to concentrate the large particle fraction in the minor flow, but also to clean the major flow from large particles. This second function is also useful in the case of focusing virtual impactors and is therefore incorporated in this invention. A suitably designed series of focusing contractions can be used for purposes other than focusing a wide range of particle sizes. For instance, it can also be arranged to achieve an unusually sharp focus for a narrow range of particle sizes. In this alternative embodiment of the invention, the particles pass through a first contraction, as a result of which they enter the next contraction in the region close to the axis. Focusing taking place in this second contraction is therefore relatively free from geometric aberration, thus producing a very sharp focus. This situation requires that a given particle size be effectively focused in two different contractions, and will therefore be termed coupled focusing. It can be achieved, for instance, by designing the first contraction such that its optimal focusing $S_m$ (the one at the minimum in FIG. 3) is larger than the Stokes of the selected particles, while the second contraction is designed such that optimal focusing $S_m$ in the second contraction is smaller than the Stokes of the selected particles. This desired situation would be reached, for instance, by a particle whose S value is approximately at the intersection of the two curves (1, 2) shown in FIG. 4 for two subsequent contractions. More than two contractions can be used to further reduce geometric aberration, to approach more closely the ideal situation of an infinitely sharp focus. While this singular focusing effect is restricted to a modest range of particle sizes, this embodiment is useful to separate particles having these special sizes from larger and smaller sizes. FIG. 12 illustrates the diameter of the focused beam (normalized with the nozzle throat diameter) at a fixed axial position, as a function of S. The particle beam is formed by a composite focusing nozzle designed with two contractions, arranged as specified above to produce a very sharp focus. This singular condition arises at $S=S^*\sim50$, corresponding to the intersection of the two curves of FIG. 4. FIG. 12 represents, in a standard scientific plot, the corresponding diameter of the neck of the focused beam ($D_m$), normalized with the nozzle throat diameter, at a fixed axial position, as a function of S. Two valleys are shown in FIG. 12. The first valley (17) is caused by focusing at the most downstream constriction, at a Stokes lower than the optimal focusing S. The second and deeper valley (18) is caused by the mentioned effect of coupled focusing. When this size-selective set of focusing contractions is followed by a collector with a small orifice, as shown in FIGS. 9 and 10, the particles with S=S* (where S* stands for the Stokes of the deep valley (18) in FIG. 12) will entirely pass through the collector orifice, while the beam of larger and smaller particles will spread more and will only pass partially into the collector. Resolutions $\Delta S/S^*$ as high as 7 have been determined for this size separation device, where $\Delta S$ is the full range of S values for which the diameter of the focused beam is smaller than $2^{1/2}$ times the minimum diameter shown in FIG. 12. This resolution is adequate for many size separation purposes, but is limited by the axial symmetry of the system. Breaking this symmetry enables substantially higher resolving powers. This can be done, for instance, by introducing a slight curvature in the imaginary line defining the center of the various focusing contractions.

Other variants of the invention can be achieved by those skilled in the art to achieve purposes other than size selection, concentration over a wide size range, or concentration over a narrow size range. For example, different particles with different diameters may be sharply focused at different positions, on-axis or off-axis, whereby they can be separated according to size while each size is highly concentrated at its own focal point.

The invention claimed is:

1. A method to concentrate particles of one or several sizes suspended in a gas, the method comprising:
    sampling a large flow rate of said gas; and,
    passing said sampled gas flow through an aerodynamically focusing nozzle, such that some among said particles are focused into a small focal region,
    wherein said focusing nozzle includes at least two contractions including, in immediate succession, a concave region and a convex region, said flow of gas passing first through said concave region and then through said convex region, said contractions being configured such that said flow of gas is accelerating through most of its path from the first to the last among said at least two contractions, and such that said flow of gas does not separate when the Reynolds numbers in at least two of said at least two contractions exceeds 150.

2. The method of claim 1, wherein at least one among said at least two contractions accelerates continuously said flow.

3. The method of claim 1 further comprising locating a collector piece with a collection orifice in the vicinity of said focal region, such that said focused particles penetrate through said collection orifice.

4. The method of claim 3, wherein a small fraction of said flow of gas is sampled as a minor flow through said collection orifice, together with a substantial fraction of said focused particles.

5. The method of claim 4, wherein said focused particles sampled through said collecting orifice are heated such as to release vapors, and said vapors are carried by said sampled minor flow for analysis in a suitable instrument.

6. The method of claim 5, wherein said suitable instrument includes a mass spectrometer.

7. The method of claim 5, wherein said suitable instrument includes a differential mobility analyzer.

8. The method of claim 4, wherein the flow of gas not sampled through said collecting orifice is drawn free from large particles for further use.

9. The method of claim 8, wherein said flow free from large particles is analyzed in a suitable instrument.

10. The method of claim 3 further comprising providing a small stream of counterflow gas exiting said collection orifice, moving towards said at least two contractions.

11. The method of claim 3 further comprising protecting said collection orifice from being obstructed by large particles by including upstream from the focusing nozzle a cyclone, a sieve, or other device for selective elimination of large particles.

12. The method of claim 1 further comprising locating a target surface in the vicinity of said focal region, such as to be modified by said focused particles.

13. The method of claim 12, wherein said focused particles are abrasive, and said target surface is modified by being cut or eroded by said focused particles.

14. The method of claim 1 further comprising probing said focused particles in said focal region with radiation.

15. The method of claim 1, wherein the flow of gas exiting said focusing nozzle is further passed through a diffuser for pressure recovery.

16. The method of claim 1, wherein most particles having a given Stokes number S are contained in said focal region within a cross section smaller than 25% of the narrowest cross section of said focusing nozzle.

17. The method of claim 16, wherein most particles having a given Stokes number S are contained in said focal region within a cross section smaller than 1% of the narrowest cross section of said focusing nozzle.

18. The method of claim 16, wherein the axial position of said focal region is substantially independent of the Stokes number over a range of Stokes numbers.

19. The method of claim 18, wherein said Stokes number range includes all Stokes numbers between a maximum value and a minimum value, such that the ratio between said maximum value and said minimum value exceeds 10.

20. The method of claim 1, wherein the method is operated at reduced pressure.

21. The method of claim 1, wherein said contractions includes a second concave region immediately adjacent said convex region, said flow path continuously converging across said concave region, said convex region and said second concave region.

* * * * *